United States Patent
Foster et al.

(10) Patent No.: US 6,832,682 B1
(45) Date of Patent: Dec. 21, 2004

(54) ORTHOPAEDIC BONE CEMENT MIXING CONTAINER

(75) Inventors: David Foster, Woodstock (GB);
Anthony Jones, Abingdon (GB);
Rebecca Eveleigh, Cheltenham (GB)

(73) Assignee: Summit Medical Limited, Gloucestershire (GB)

( * ) Notice: Subject to any disclaimer, the term of this patent is extended or adjusted under 35 U.S.C. 154(b) by 0 days.

(21) Appl. No.: 10/069,081

(22) PCT Filed: Jul. 26, 2000

(86) PCT No.: PCT/EP00/07204

§ 371 (c)(1),
(2), (4) Date: Aug. 12, 2002

(87) PCT Pub. No.: WO01/06963

PCT Pub. Date: Feb. 1, 2001

(30) Foreign Application Priority Data

Jul. 27, 1999 (GB) .............................. 9917624

(51) Int. Cl.[7] .............................................. B65D 25/08
(52) U.S. Cl. ...................................................... 206/219
(58) Field of Search ................................ 206/219–222, 206/568; 366/139, 256; 215/DIG. 8, 6, 10; 53/409, 452, 467, 476

(56) References Cited

U.S. PATENT DOCUMENTS

| | | | |
|---|---|---|---|
| 3,156,369 A | * 11/1964 | Bowes et al. | ............... 206/222 |
| 3,840,136 A | * 10/1974 | Lanfranconi et al. | ....... 206/222 |
| 4,015,945 A | 4/1977 | Frankel | |
| 4,185,072 A | 1/1980 | Puderbaugh et al. | |
| 4,195,731 A | * 4/1980 | Cavazza | ..................... 206/222 |
| 4,758,096 A | * 7/1988 | Gunnarsson | ................ 366/139 |
| 5,029,718 A | * 7/1991 | Rizzardi | ..................... 206/222 |
| 5,038,951 A | * 8/1991 | Rizzardi | ..................... 206/222 |
| 5,114,240 A | * 5/1992 | Kindt-Larsen et al. | ...... 366/139 |
| 5,474,209 A | * 12/1995 | Vallet Mas et al. | ......... 206/221 |
| 6,148,996 A | * 11/2000 | Morini | ....................... 206/222 |

FOREIGN PATENT DOCUMENTS

| | | |
|---|---|---|
| DE | 36 40 279 A | 6/1987 |
| EP | 0 178 658 A | 4/1986 |
| EP | 0 397 589 A | 11/1990 |
| WO | WO 87/05492 | 9/1987 |
| WO | WO 93/10892 | 6/1993 |
| WO | WO 95/22402 | 8/1995 |
| WO | WO 95/18031 | 5/1997 |
| WO | WO 97/18031 | 5/1997 |

\* cited by examiner

Primary Examiner—Luan K. Bui
(74) Attorney, Agent, or Firm—Alix, Yale & Ristas, LLP

(57) ABSTRACT

The invention discloses a pre-filled orthopedic cement container in which the cement can also be mixed. The container comprises an outer housing defining the mixing chamber and an inner housing containing the cement prior to mixing. The inner housing is removable, prior to mixing, in such a way that the cement powder remains in the mixing chamber for mixing.

20 Claims, 3 Drawing Sheets

ORTHOPAEDIC BONE CEMENT MIXING CONTAINER

This application is the U.S. National Phase of International Application No. PCT/EP00/07204, filed on Jul. 26, 2000.

BACKGROUND OF THE INVENTION

This invention relates to a container in which orthopaedic bone cement is mixed.

Orthopaedic bone cement is used throughout the world to secure hip, knee and other metallic protheses in an appropriate anatomical position.

Many different systems are available for mixing orthopaedic bone cement and the type of: apparatus selected will depend on the personal preferences of the doctor or nurse mixing the cement, as well as the amount of cement being mixed and the type of materials being used Essentially, orthopaedic cement its made up of a powder component, e.g. polymethylmethacrylate powder, and a monomer, eg. g. methylmethacrylate monomer liquid, generally provided in an ampoule which is broken and added to the powder. The two components are then thoroughly mixed to provide a malleable cement which can be manipulated and applied to the appropriate bone parts, during surgery.

In order to avoid the cement becoming brittle, it is essential that the two components are very thoroughly mixed together and no 'dry' or 'dead' spots remain. Furthermore, as most cements set fairly quickly, it is important that the mixing can be quickly and easily carried out. This is, also, of course important as surgery should be carried out as quickly as possible for the comfort and safety of the patient.

Originally, the cement components were mixed, by hand, using a bowl and spatula. A theatre nurse would mix the appropriate quantities of the two components in the bowl and the physician would then cake some of the mixed cement and mould it to the required shape, before inserting it into a preformed cavity or applying it to a resected bony surface where the prothesis is to be positioned. Cement may either be applied by hand or may be put into a syringe and applied thereby.

Although mixing in thin way is straightforward and convenient, it can have drawbacks.

Firstly, free methylmethacrylate fumes"are emitted from the mixture. It is desirable to remove these fumes, or prevent them from escaping into the atmosphere, since they have an unpleasant odour and may be harmful to operating room and personnel. The fumes are known to cause nausea and giddiness and are generally objectionable, particularly to the nurses who actually carry out the mixing.

Secondly, a very high mixing efficiency is required to produce a homogenous cement material. During the mixing process, air is naturally introduced into the mixture since air is inherently existent within the powder and also in and around the mixing vessel. Air bubbles are also produced by the 'boiling off' of monomer which occurs during the mixing process. The introduction of air produces a weak cement and, since the joint must usually support a heavy load, it is important to reduce the amount of air in the mixture as much as possible in order to improve the mechanical strength of the cement material.

Furthermore, this mixing process can be slow and result in the cement beginning to dry cut before it has been used and can require the patient to be on the operating table longer than desirable. Where particularly viscous cements are used, mixing in this way can also be rather tiring for the theatre nurse and can, in some cases, lead to muscle fatigue and strain.

A variety of systems is now available to simplify and improve the mixing of bone cement and to overcome the problems mentioned above. Many of these include the application of a vacuum to a sealed mixing chamber which removes air from the mixture and avoide weak spots. This results in a greatly improved cement.

One such mixing device is the bowl mixer forming the subject of European Patent No. 0616552. This system is preferred by many users as it is small and convenient to use and the mixing action is similar to that carried out in the above described manual bowl mixing technique and is one with which nurses are generally familiar.

Another mixing system is described in European Patent No. 0744991. In this arrangement, the cement in mixed in a cylindrical mixing chamber. The mixing mechanism comprises paddles rotatably mounted within the chamber. The paddles are rotated around the chamber by means of a 'barley twist' mechanism so that the user merely has to push the handle up and down, to cause rotation of the paddle. Furthermore, once the cement is is mixed, this system can be converted into: a syringe type dispenser by addition of a nozzle and plunger. There is thus no need to remove the mixed cement from the nixing chamber and transfer it to a dispenser.

Other similar mixing arrangements are known.

In all of these systems, the cement components need to be put into the mixing chamber. Generally, the nurse in provided with the cement powder, in a bag, and monomer ampoule. These are opened by the nurse, manually, and are introduced into the mixing chamber or bowl by means of funnels.

One problem is that when cutting open the cement powder bag and inserting the powder via the funnel, there is a certain degree of wastage due to spillage and cement clinging to the funnel. Furthermore, the opening and pouring of the cement powder caused a powder cloud which, within the regulated confines of the operating theatre, is unpleasant and may even have adverse effects on the theatre personnel.

These problems become more acute when time is very short and the mixing must be done extremely quickly, or with inexperienced theatre personnel.

One solution which has been considered is to provide a pre-filled mixing apparatus, wherein the disposable mixer, for example a bowl mixer or syringe mixer as described above, is supplied already containing the cement powder in the mixing chamber. This generally makes things much easier for the theatre nurse when needing to mix the cement quickly during an operation.

However, tents have shown that if the cement powder is housed within the mixing chamber or bowl and contained therein by means of a cap, the powder moves about, particularly during transportation, and covers the entire internal surface area of the mixing chamber and the lid. When the mixing is carried out, with the introduction of the monomer, unmixed powder remains at the top of the mixing vessel due to the monomer not wetting all of the walled surface, and the mixing paddle not reaching the very fine layer of powder on the walls and at the top of the chamber. Thus, powder is wasted and 'dry' spots occur, resulting in brittle cement which can have adverse consequences.

The aim of the present invention it to provide a pre-filled orthopaedic cement mixing apparatus in which the above mentioned problems are overcome.

SUMMARY OF THE INVENTION

According to one aspect of the present invention, there is provided an apparatus for containing and mixing orthopaedic cement, the apparatus containing an outer housing defining a mixing chamber and an inner housing containing the cement prior to mixing, wherein the inner housing is removable from the outer housing such that the cement remains in the mixing chamber.

In accordance with another aspect of the invention, there is provided a method of providing and mixing of orthopaedic cement comprising sealing said cement in an inner housing; disposing said inner housing within an outer housing which defines a mixing chamber; removing the inner housing, leaving the cement in the mixing chamber for mixing.

The present invention may be incorporated into any known cement mixing arrangements including the bowl mixer and syringe mixer described above. It may also be incorporated in mixing bowls where the mixing is carried out simply using a spatula etc.

The inner housing may be removable from the outer housing in any way, for example it may be in the form of a bag which is merely lifted out by the user, which opens on removal to drop the cement powder into the mixing chamber. In the most preferred embodiment, however, the inner housing is attached to or formed integrally with a lid provided on the container. The inner housing and the lid may, for example, be attached to each other by a snap fit arrangement or, indeed, by any other means of attachment. Thus, when the cement is is to be mixed, the lid is removed by the user and as the lid is removed, it takes with it the inner housing.

To provide a secure container during transportation etc., the lid is preferably attached to the outer housing by means of a screw thread. Seals may also be provided.

The inner housing may be made of any materials suitable for containing the cement powder. Preferably, the material of which the inner housing; is made is less rigid than that of the outer housing. This allows the inner housing to be compressed against the outer housing to provide a good seal at the open end of the inner housing.

It is important that, prior to removal of the inner housing, the cement is securely contained within the housing and, therefore, the 'open' end of the inner housing should form a seal with the outer housing or should be closed after filling.

Thus, in one embodiment, not shown, the inner housing has an open end into which the cement is inserted. This open end is then closed by any suitable means and the inner housing is placed within the outer housing in such a manner that when the inner housing is removed from the outer housing, the inner housing is opened or ruptured allowing the cement to fall out into the inner housing.

In the most preferred arrangement, the inner housing, at the open end, is provided with a feather seal edge which provides a seal against the base or lower part of the outer housing

BRIEF DESCRIPTION OF THE DRAWINGS

Preferred embodiments of the invention will now be described, by way of example only, with reference to the accompanying drawings.

DETAILED DESCRIPTION OF THE PREFERRED EMBODIMENTS

Figure 1:
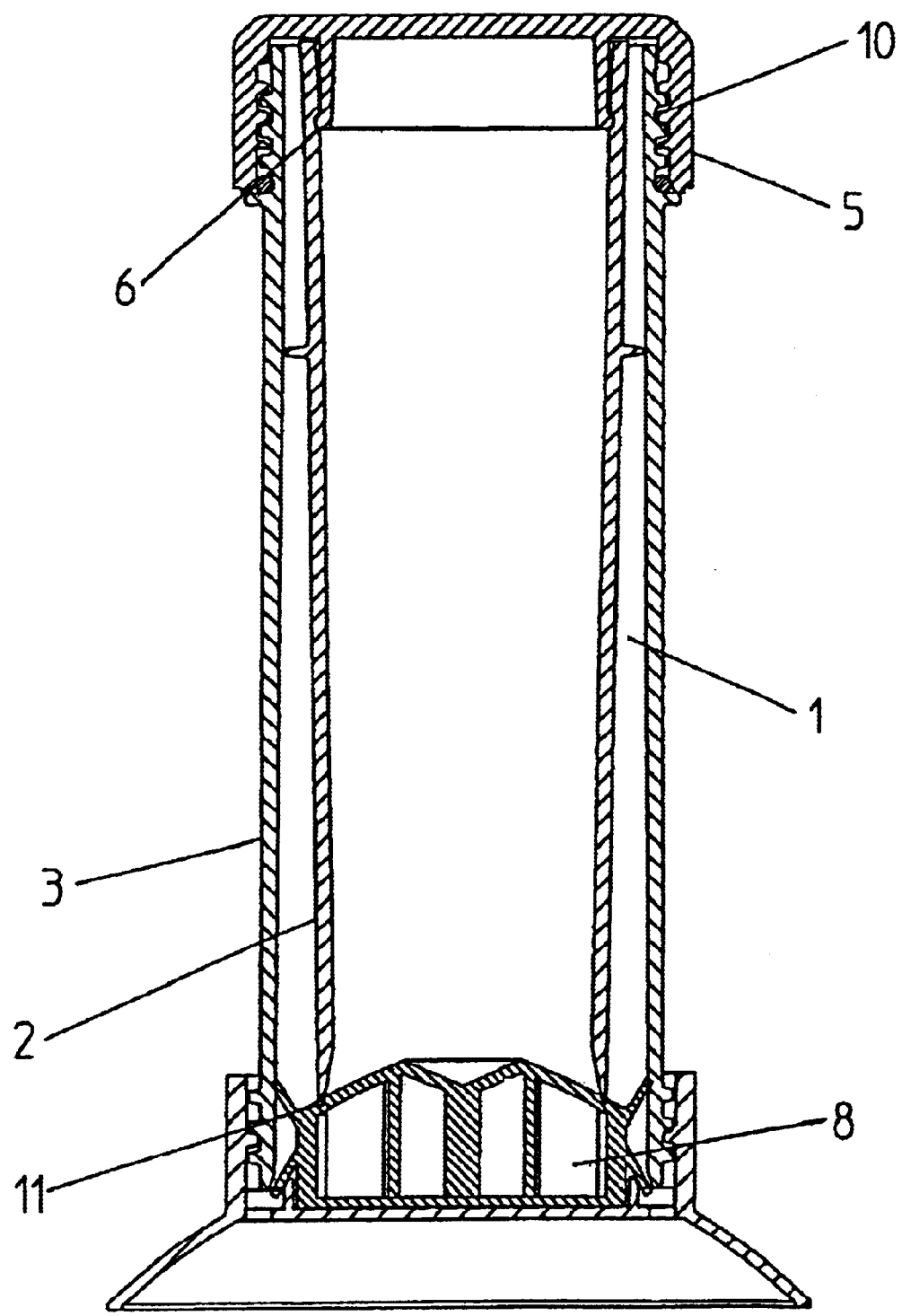
FIG. 1 shown a cross-section of a mixing system according to the present invention.

The embodiment shown 1 in FIG. 1 uses a mixing system such as described in EP 0744991. This comprises a cylindrical mixing chamber, in which is arranged a mixing paddle (not shown), rotated by means of a handle connected thereto by a 'barley twist' rod and gear mechanism. The paddle is rotated around the mixing chamber by a pushing and pulling action on the handle. Vacuum is applied to the chamber during the mixing. Once the cement is mixed, the cap and mixing mechanism are removed and replaced by a nozzle. A plunger is applied to the other end of the mixing chamber and is pushed through the chamber, by means of, e.g., a mastic-type gun to eject the mixed cement through the nozzle.

This mixing system is modified by the present invention and is provided as a pre-filled system.

Thus, the cement is provided in an inner housing 2 which is located in the outer, mixing chamber housing 3.

The inner housing, containing the cement 4, is attached to the cap 5 of the mixing chamber by a snap fit arrangement 6. This creates a seal through which the cement powder cannot pass.

Figure 2:
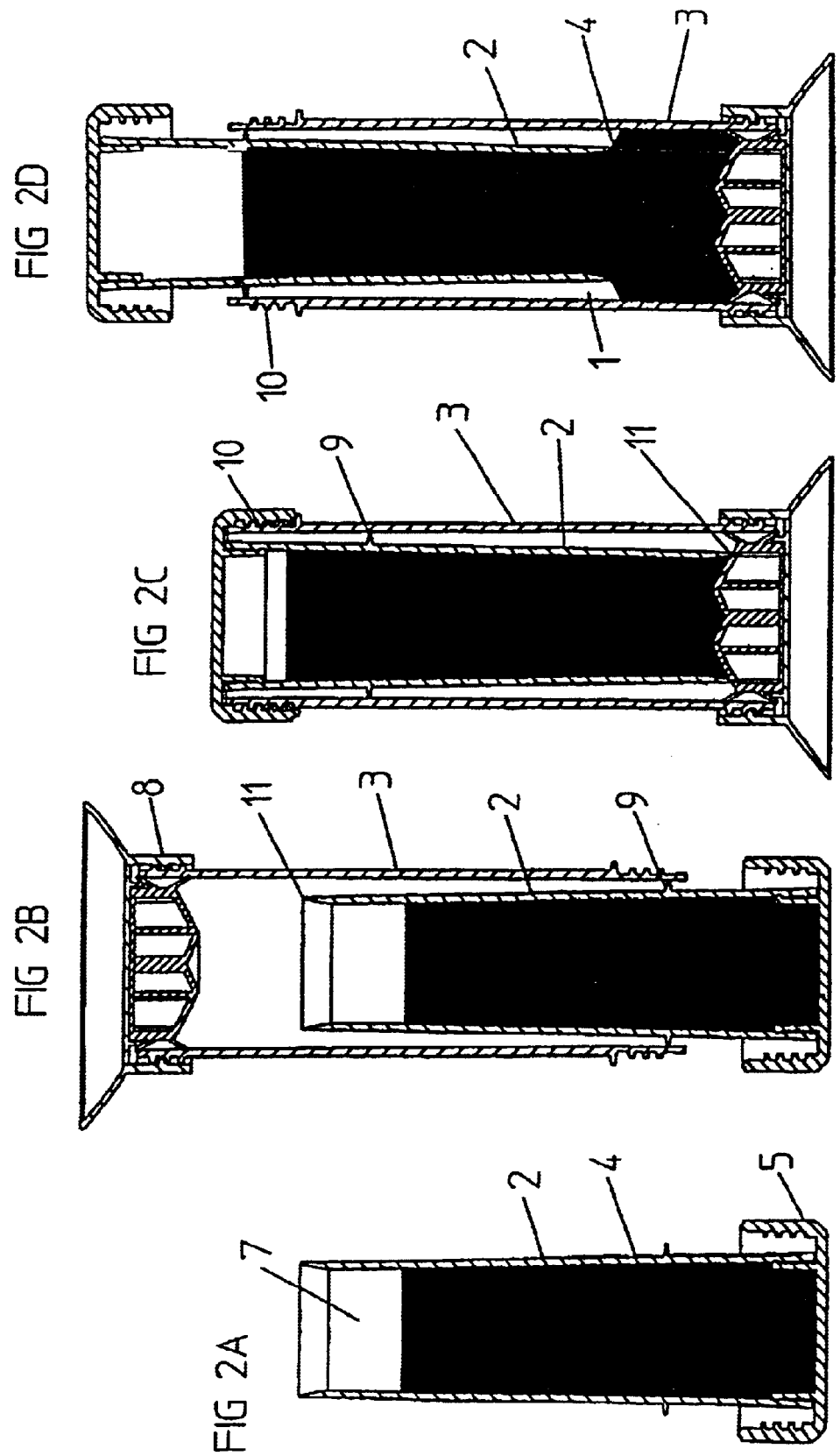
FIGS. 2A–2D show the different stages of inserting and mixing the cement using the apparatus shown in FIG. 1

FIG. 2A shows how the cement is inserted into the inner housing, via the open end 7 of the housing.

The outer housing 3 incorporating the piston and base 8 is then fitted over the cement containing inner housing as shown in FIG. 2D.

Guide lips 9 may be provided on the outer surface of the inner housing to assist in the correct positioning of the outer housing relative to the inner housing.

The outer housing is then secured to the cap, by means of a screw thread 10, as shown in FIG. 2C. The open end of the inner housing, containing the cement, is provided with a seal 11, preferably a feather seal, which fully seals to the piston part of the outer housing to secure the cement powder within the inner housing. This results in a fully sealed packaged container, containing the cement powder within the inner housing, ready for use. The whole device is then packaged and sterilised for use.

A breather pad (not shown) may be provided on the cap no as to allow gas circulation to the cement.

As shown in FIG. 2D, when the cement is to be mixed, the user unscrews the cap 5 from the outer housing 2 and lifts away the cap and the inner housing 3 connected thereto. As the inner housing is lifted away from the base of the outer housing, the cement powder 4 drops out of the inner housing into the mixing chamber 1. The cap and inner housing are then discarded and the standard mixing procedure for this type of mixing arrangement is carried out.

Figure 3:
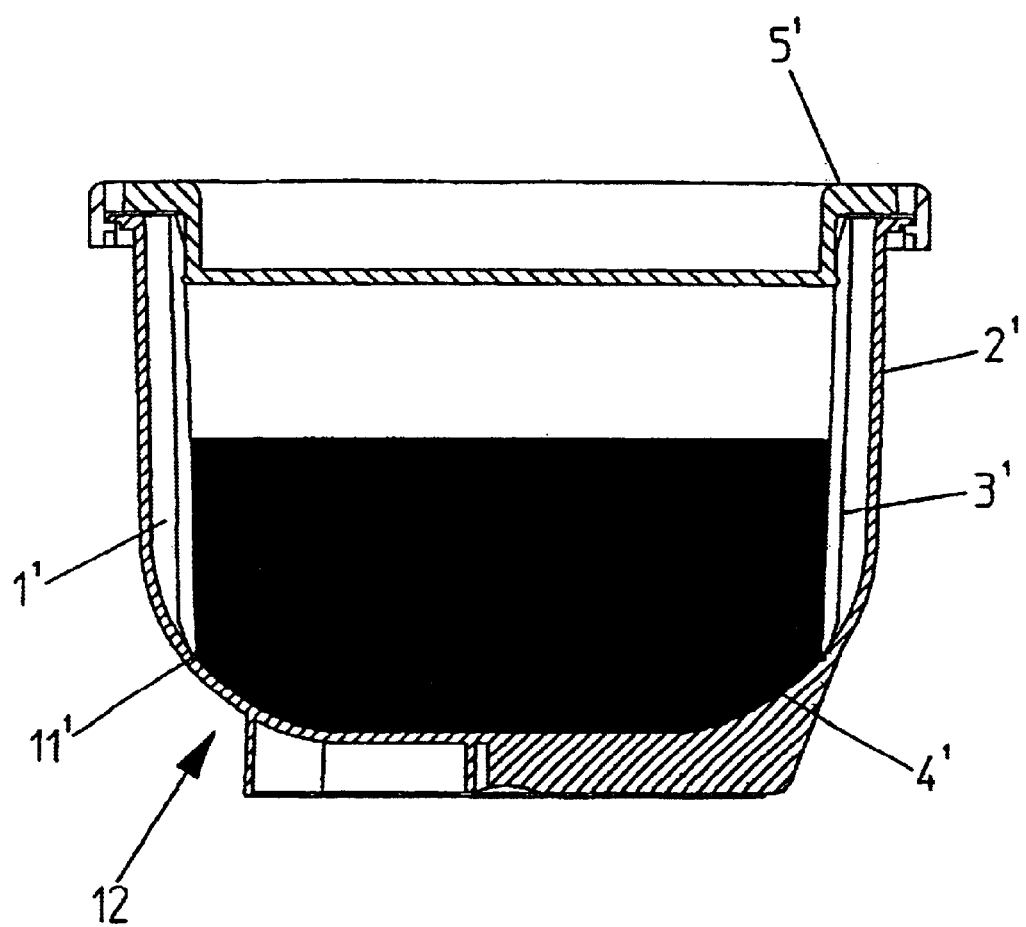
FIG. 3 shows an alternative embodiment of the present invention

A similar procedure is used in relation to other mixing arrangements such as the bowl mixer 12 shown in FIG. 3. This may be a bowl as described in BP 0616552. The principle is essentially the same. An inner housing 3', containing the cement powder 4', is attached to the lid 5' of the bowl at one end and is sealed 11' to the base of the bowl or the sides of the bowl near its base by means of e.g. a feather seal. In use, the lid 5' and attached inner housing 3' are removed, such that the cement powder 4' drops out of the inner housing into the mixing chamber 1 and mixing is carried out in the usual way.

It is preferable that the inner housing is made of a material which is less rigid than the outer housing. This allows the feather seal edge of the inner housing to be compressed unto the outer housing to provide a secure seal for the cement powder.

In the preferred syringe type arrangement, the inner housing is designed to hold up to 80 g of cement powder, i.e. a double mix of cement. In the case of the bowl mixer, preferably, the inner housing can hold up to 120 g, i.e. a triple mix of cement.

Because the cement powder is contained within the inner housing until it is to be mixed, find in then dropped out of the housing only into the bottom of the mixing chamber, no cement clings to the upper outer walls of the mixing chamber and so practically all of the cement can be thoroughly mixed, producing a high quality mixed orthopaedic cement.

What is claimed is:

1. An apparatus for containing a powder component and mixing the powder component with a liquid component to form an orthopedic cement, the apparatus comprising:
   an outer housing defining a mixing chamber having an inside surface; and
   an inner housing defining a powder component storage chamber containing the powder component, said powder component storage chamber having an open end surrounded by a sealing edge, said inner housing secured to said outer housing with said sealing edge in sealing contact with said inside surface to close the open end of said powder component storage chamber, said inner housing being removable from said outer housing to open said powder component storage chamber and release said powder component into said mixing chamber.

2. An apparatus as claimed in claim 1, wherein the outer housing is provided with a cap and wherein the inner housing is attached to said cap such that the cap and inner housing can be removed from the outer housing together.

3. An apparatus as claimed in claim 2 wherein the cap is attached to the outer housing be means of a screw thread.

4. An apparatus as claimed in claim 2, wherein the inner housing is attached to the cap by means of a snap fit arrangement.

5. An apparatus as claimed in claim 1, wherein said sealing edge is a feather tip seal for sealing against said inside surface.

6. An apparatus as claimed in claim 1, wherein said inner housing is less rigid than said outer housing.

7. An apparatus as claimed in claim 1, wherein said outer housing is in the form of a cylindrical mixing chamber adapted to be provided with a mixing mechanism comprising a blade arrangement rotatable around said mixing chamber.

8. An apparatus as claimed in claim 1, wherein said outer housing is in the form of a bowl shaped mixing chamber adapted to be provided with a mixing mechanism comprising a blade arrangement rotatable around said mixing chamber.

9. An apparatus as claimed in claim 1, further comprising means allowing gas to circulate around the powder component contained in the inner housing.

10. An apparatus as claimed in claim 3, wherein the inner housing is attached to the cap by means of a snap fit arrangement.

11. An apparatus as claimed in claim 2, wherein said sealing edge is a feather tip seal for sealing against said inside surface.

12. An apparatus as claimed in claim 2, wherein said inner housing is less rigid than said outer housing.

13. An apparatus as claimed in claim 2, wherein said outer housing is in the form of a cylindrical mixing chamber adapted to be provided with a mixing mechanism comprising a blade arrangement rotatable around said mixing chamber.

14. An apparatus as claimed in claim 2, wherein said outer housing is in the form of a bowl shaped mixing chamber adapted to be provided with a mixing mechanism comprising a blade arrangement rotatable around said mixing chamber.

15. An apparatus as claimed in claim 2, further comprising means allowing gas to circulate around the powder component contained in the inner housing.

16. An apparatus as claimed in claim 3, wherein said sealing edge is a feather tip seal for sealing against said inside surface.

17. An apparatus as claimed in claim 3, wherein said inner housing is less rigid than said outer housing.

18. An apparatus as claimed in claim 3, wherein said outer housing is in the form of a cylindrical mixing chamber adapted to be provided with a mixing mechanism comprising a blade arrangement rotatable around said mixing chamber.

19. An apparatus as claimed in claim 3, wherein said outer housing is in the form of a bowl shaped mixing chamber adapted to be provided with a mixing mechanism comprising a blade arrangement rotatable around said mixing chamber.

20. A method for containing and releasing a powder component of an orthopedic cement comprising:
   disposing said powder component in a powder component storage chamber defined by an inner housing, said chamber having an open end surrounded by a sealing edge;
   securing said inner housing to an outer housing defining a mixing chamber with an inside surface, said sealing edge in sealing contact with said inside surface to close said open end of said powder component storage chamber; and
   removing said inner housing from said outer housing, thereby separating said sealing edge from said inside surface to release said powder component into said mixing chamber.

* * * * *